US006621581B1

(12) United States Patent
Hunt et al.

(10) Patent No.: US 6,621,581 B1
(45) Date of Patent: Sep. 16, 2003

(54) METHOD AND APPARATUS FOR MAPPING SURFACE TOPOGRAPHY OF A SUBSTRATE

(75) Inventors: James David Hunt, Charlotte, NC (US); Lee Dante Clementi, Lake Wylie, SC (US); Charles A. Monjak, Clover, SC (US)

(73) Assignee: ADE Corporation, Westwood, MA (US)

( * ) Notice: Subject to any disclaimer, the term of this patent is extended or adjusted under 35 U.S.C. 154(b) by 0 days.

(21) Appl. No.: 09/418,722

(22) Filed: Oct. 15, 1999

Related U.S. Application Data
(60) Provisional application No. 60/104,490, filed on Oct. 16, 1998.

(51) Int. Cl.[7] .............................................. G01B 11/24
(52) U.S. Cl. ...................................................... 356/601
(58) Field of Search ................................ 356/601–609, 356/237.1–237.5; 250/559.22, 559.4

(56) References Cited

U.S. PATENT DOCUMENTS

| | | |
|---|---|---|
| 4,364,663 A | 12/1982 | Gardner et al. |
| 4,511,800 A | 4/1985 | Harbeke et al. |
| 4,844,616 A | 7/1989 | Kulkarni et al. |
| 4,859,062 A | 8/1989 | Thurn et al. |
| 5,046,847 A | 9/1991 | Nakata et al. |
| 5,189,481 A | 2/1993 | Jann et al. |
| 5,383,025 A | 1/1995 | Forrest |
| 5,436,464 A | 7/1995 | Hayano et al. |
| 5,708,279 A | 1/1998 | Cheng |
| 5,712,701 A | 1/1998 | Clementi et al. |
| 5,883,710 A | 3/1999 | Nikoonahad et al. |
| 5,903,342 A | 5/1999 | Yatsugake et al. |
| 5,923,430 A | * 7/1999 | Worster et al. .......... 356/237.2 |
| 6,046,801 A | * 4/2000 | Liu et al. .................. 356/237.1 |

FOREIGN PATENT DOCUMENTS

WO   WO 97/26529   7/1997

OTHER PUBLICATIONS

Ferrara, M.B. et al., *Reconvergent Specular Dtection of Material Defects on Silicon*, 1995 IEEE/SEMI Advanced Semiconductor Manufacturing Conference, Nov. 13, 1995, pp. 136–140.

Wu, Zhongquan and Li, Lingxiao, *A Line–Integration Based Method for Depth Recovery from Surface Normals*, Computer Vision, Graphics, and Image Processing, 1988, vol. 43, pp. 53–66.

\* cited by examiner

*Primary Examiner*—Tu T. Nguyen
(74) *Attorney, Agent, or Firm*—Alston & Bird LLP (57) ABSTRACT

Full surface maps of slope and height are determined for the surface of a highly smooth surface such as a silicon wafer, by an apparatus which includes a light source for creating a light beam and scanning and wafer transport systems which cause the incident beam to be scanned over the full surface of the wafer. A quad cell light detector is positioned to receive the beam specularly reflected from the wafer surface, the quad cell detector having four cells arranged in quadrants with each cell providing an electrical signal indicative of the amount of light received by the cell. A processor is programmed to calculate changes in spot location on the detector based on the signals from the cells, and to calculate changes in surface slopes based on the changes in spot location. Full maps of X- and Y-slope are produced, and a line integration algorithm is used for calculating full surface height maps. Regions of surface height gradient exceeding a threshold are flagged as defects by the processor.

18 Claims, 8 Drawing Sheets

METHOD AND APPARATUS FOR MAPPING SURFACE TOPOGRAPHY OF A SUBSTRATE

CROSS-REFERENCE TO RELATED APPLICATION

This application claims the benefit of the filing date of U.S. Provisional patent application Ser. No. 60/104,490 filed Oct. 16, 1998.

FIELD OF THE INVENTION

The present invention relates to optical inspection apparatus and methods for inspecting the surface of a silicon wafer or other substrate. More particularly, the invention relates to an apparatus and methods for mapping the topography of a surface of a wafer or other substrate, and for identifying defect regions of the substrate based on a topographical map of its surface.

BACKGROUND OF THE INVENTION

In a variety of applications it is desirable to be able to produce a map of the topography of a surface in situations where mechanical means for mapping the surface are impractical or inadequate. Particularly in the case of a highly polished surface having very small undulations or deviations from an ideal perfectly flat surface, mechanical measuring devices are generally incapable of providing the degree of resolution required to accurately map such a surface, and also may cause damage to the surface. Accordingly, non-contact means for mapping such a surface are preferred.

For instance, manufacturers of integrated circuits are constantly striving to reduce the line widths of conductors laid down on the surface of a silicon wafer to form integrated circuits. Currently, lines widths as narrow as 0.18 $\mu$m are being used, and it can be expected that the line widths will continue to be reduced. Reduced line widths cause severe depth of focus limitations in the lithography process. Surface undulations, when combined with the reduced depth of focus, can cause the lines to be laid down inaccurately. Accordingly, the lithography process as well as other considerations create a need to minimize surface irregularities of the starting silicon wafer.

Because the surface quality of the wafer is an important ingredient in the quality of the resulting integrated circuits, inspection devices and methods are needed for detecting surface irregularities that might cause a defective circuit to be produced. It will be appreciated that even very slight deviations from a perfectly flat surface may be too large to be tolerated, particularly where the line widths being laid on the wafer are very small. Thus, there is a need for an apparatus and method capable of mapping with extremely fine resolution the surface topography of a highly smooth surface such as a silicon wafer surface. For example, it would be desirable to be able to map a wafer surface with a height resolution on the order of about 10 nm or less, and with a spatial resolution (in the in-plane direction of the wafer) on the order of about 200 $\mu$m or less.

Optical inspection devices and methods have been developed for detecting the presence and sizes of defects in and on the surface of a polished substrate, for example for use in the production of silicon wafers, and defect sizes on the order of a few tens of nanometers can be detected. Among the known commercially available apparatus for mapping the topography of a wafer, however, the best height resolution that is achieved is about 20 nm or perhaps slightly less, and the best spatial resolution is on the order of several millimeters. There is currently no known apparatus available commercially that is capable of producing a complete map of the surface topography of a highly smooth surface such as that of a silicon wafer with a very fine spatial resolution (e.g., about 200 $\mu$m or less) and an extremely fine height resolution (e.g., about 10 nm or less).

SUMMARY OF THE INVENTION

The present invention provides apparatus and methods enabling production of a complete topographical map (also referred to herein as a height map) of a highly smooth surface of a substrate such as a wafer, and for identifying defect regions of the surface based on a topographical map. Thus, in a preferred embodiment of the invention, a mapping apparatus comprises a light source adapted to produce an incident light beam and positioned to direct the incident beam to impinge on the surface and specularly reflect therefrom, a scanning system operable to move at least one of the substrate and the incident beam so as to move the incident beam in relation to the substrate such that the incident beam is impinged on the surface at a plurality of spaced-apart points to create a specularly reflected beam from each of the points, a light detector which receives each of the specularly reflected beams and provides a signal as a function of a change in location of each of the reflected beams relative to a reference location, and a processor which receives the signal corresponding to each of the points on the surface and calculates based on each signal a change in slope of the surface at each point relative to a reference slope which corresponds to the reference location of the reflected beam. The slope change information is then converted into a height map of the entire surface.

The invention further provides a method whereby defect regions on the wafer surface are identified based on a given height map defined by an array of grid points each having an associated height value, regardless of how the height map is derived. The method entails calculating, at each of the grid points of the height map, a change in surface height over a predetermined distance along the surface in a plurality of different in-plane directions of the wafer. The height change in each of the different directions is compared to a predetermined threshold. If any of the height changes in any of the directions exceeds the predetermined threshold, the grid point is identified as a defect region.

With respect to the apparatus aspect of the invention, the scanning system preferably is operable to scan the incident beam across the surface along a first direction such that the incident beam is reflected from an array of points on the surface that are spaced predetermined distances apart from each other along the first direction. The processor is operable to calculate changes in slope in the first direction for each of the points and to calculate relative surface heights of the points based on the changes in slope in the first direction. The scanning system similarly is operable to scan the beam across the surface in a second direction that is different from the first direction such that the beam is reflected from an array of points spaced apart along the second direction, thereby defining a two-dimensional grid of points. The first and second directions advantageously are perpendicular to each other, although they do not necessarily have to be so. For example, a skewed grid can be used in the present invention. Other geometrical arrays of points can also be used, as long as the array covers the whole wafer surface and adjacent points are spaced close enough together to provide the degree of spatial resolution that is desired. The scanning system can scan the beam in the first and second directions by keeping the substrate stationary and moving the beam, by moving the substrate and keeping the beam fixed, or by a combination of moving the substrate while also moving the beam.

In one preferred embodiment, the scanning system of the apparatus includes a transport mechanism operable to move the substrate so as to effect scanning of the beam over the surface. Advantageously, the transport mechanism is operable to translate the substrate along the second direction and the scanning system is operable to periodically scan the incident beam across the surface in the first direction. However, other devices and methods may be used for impinging the incident beam at a plurality of points on the surface, and the invention is not limited to any particular devices or methods for such purpose.

In accordance with a preferred embodiment of the invention, the light detector comprises a multiple-cell detector having a plurality of cells adjacently arranged, the detector providing a separate signal from each cell as a function of the amount of light intensity striking the cell. Thus, the relative strengths of the signals from the cells are indicative of the location on the detector at which the reflected beam strikes the cells. The processor receives the signals from the cells and calculates a change in location of the reflected beam based on the relative strengths of the signals. Preferably, the light detector comprises a quad-cell detector having four cells arranged in quadrants which are oriented such that the signals from the cells are indicative of surface slopes in two orthogonal X- and Y-directions along the surface. The processor preferably comprises a programmable microprocessor and is programmed to calculate surface slopes in the X- and Y-directions and to perform a line integration on the surface slopes to determine surface heights.

BRIEF DESCRIPTION OF THE DRAWINGS

The above and other objects, features, and advantages of the invention will become more apparent from the following description of certain preferred embodiments thereof, when taken in conjunction with the accompanying drawings, in which.

DETAILED DESCRIPTION OF PREFERRED EMBODIMENTS

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1:
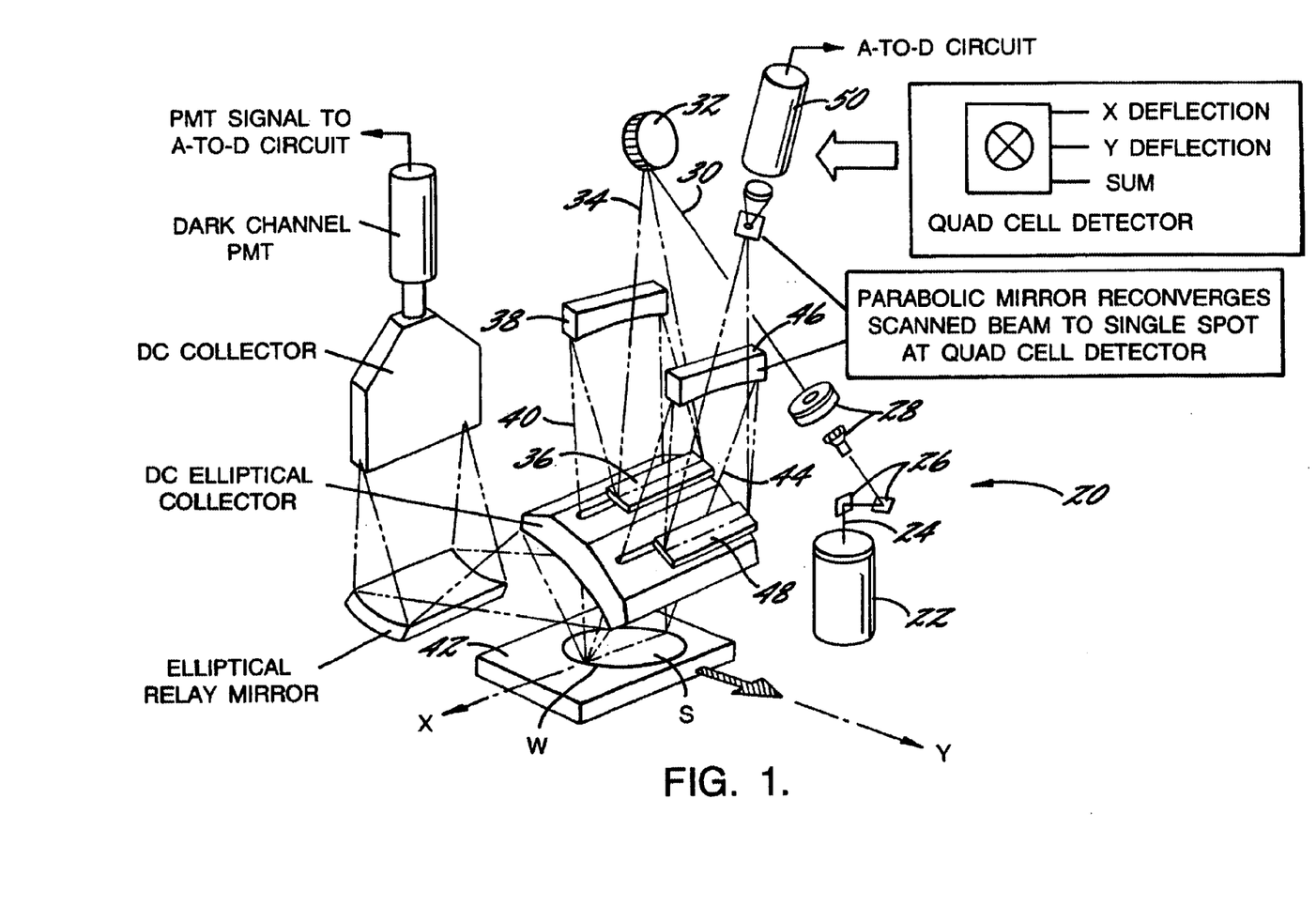
FIG. 1 is a perspective view of one preferred embodiment of an apparatus in accordance with the invention.

With reference to FIG. 1, there is illustrated an apparatus 20 for inspecting the surface quality of a substrate such as a silicon wafer. The apparatus 20 includes a light source 22 which preferably is a laser such as an argon ion laser. A light beam 24 generated by the light source 22 is directed, with the aid of mirrors 26 if desired or necessary, through spot-forming optics 28 which operate upon the beam 24 to form a highly collimated beam 30.

The apparatus 20 includes a scanning system which is operable to cause the beam 30 to be scanned across the surface S of a wafer W. The scanning system includes a rotating mirror 32 upon which the beam 30 is impinged and which reflects the beam 30 as a scanned beam 34. As shown, the scanned beam 34 sweeps through a range of angles relative to the surface S. Since it is desired that the incident beam which is impinged on the surface S have a constant incident angle throughout the scan, the scanning system also includes various optics which convert the scanned beam 34 into a beam of constant incident angle. Thus, the scanning system includes, for example, a folding mirror 36 which reflects the scanned beam 34 back to a parabolic mirror 38, which in turn reflects the beam as an incident beam 40 of constant incident angle. Accordingly, the rotating mirror 32, folding mirror 36, and parabolic mirror 38 act in concert to create an incident beam 40 which is linearly scanned across the surface S in a first direction represented by the X-axis shown in FIG. 1.

The scanning system also includes a transport mechanism 42, schematically illustrated in FIG. 1, which is operable to translate the wafer W along a second direction that is normal to the X-direction and is represented by the Y-axis. Thus, as the wafer W is translated along the Y-direction, the incident beam 40 is scanned in lines across the wafer surface S along the X-direction. As further described below, the reflected beam 44 is captured and converted into electrical signals. By periodically sampling these electrical signals synchronously with the scanning of the incident beam 40 across the surface S, properties of the reflected beam 44 can be deduced for a plurality of points that are spaced apart along the X- and Y-directions so as to form a regular array of grid points or pixels. For example, for a wafer having a diameter of about 200 mm, a grid of 1024 by 1024 pixels may be used, each pixel having a size of about 214 µm square. The incident beam 40 preferably has a spot size of about 30 µm.

A parabolic mirror 46 captures the reflected beam 44 and reflects the beam back to a folding mirror 48, which in turn reflects the beam to a quad cell detector 50. The parabolic mirror 46 and folding mirror 48 coact to reconverge the scanned beam to a single spot at the quad cell detector 50 (i.e., the beam would always strike the detector at the same spot if the surface S were perfectly flat).

Figure 2:
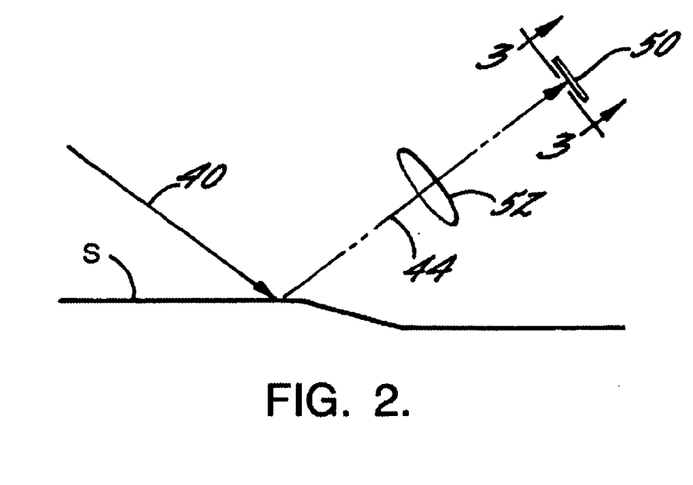
FIG. 2 is a schematic side elevational view of a substrate surface of zero or reference slope being impinged by an incident beam and showing a light detector receiving the reflected beam.
Figure 3:
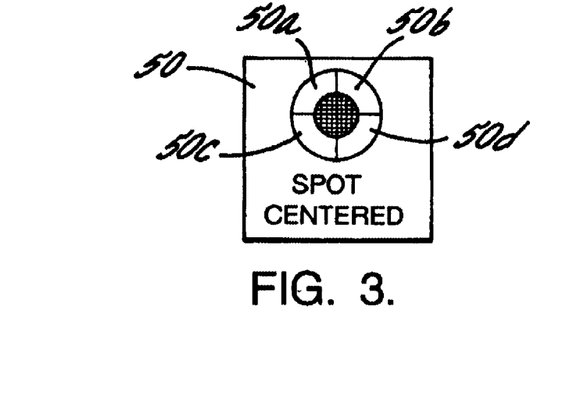
FIG. 3 is a view taken on line 3—3 of FIG. 2, showing the reflected beam spot centered on the detector when the substrate surface has a zero or reference slope value.

The quad cell detector 50 has four cells 50a–d (FIG. 3) arranged in quadrants. With reference to FIGS. 2 and 3, the quad cell detector 50 is positioned such that when the incident beam 40 strikes a portion of the surface S that has a zero slope (or some other known reference slope), the converged spot of the reflected beam 44 is centered on the detector 50 such that each of the cells 50a–d receives the same amount of light. Each of the cells 50a–d produces its own electrical signal as a function of the intensity of light striking the cell. Accordingly, the relative strengths of the four signals can be used to deduce when and to what degree the light spot is off-center.

Figure 4:
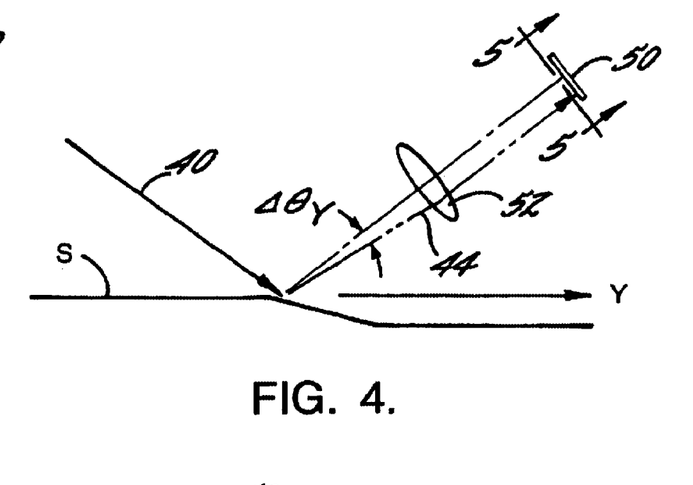
FIG. 4 is a view similar to FIG. 2, showing an incident beam impinging on a substrate surface of non-zero or non-reference slope and showing the light detector receiving the reflected beam.
Figure 5:
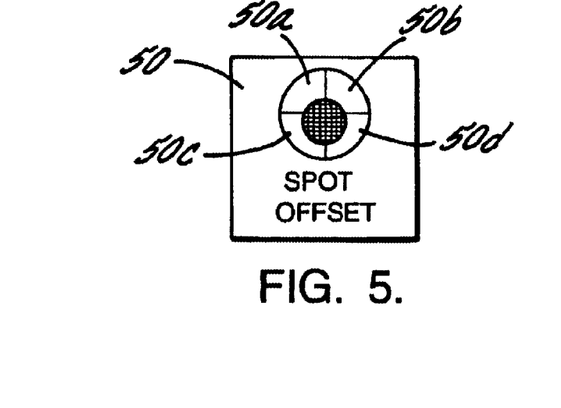
FIG. 5 is a view taken on line 5—5 of FIG. 4, showing the reflected beam spot not centered on the detector when the substrate surface has a non-zero or non-reference slope value.

More specifically, with reference to FIGS. 4 and 5, when the incident beam 40 reflects off a portion of the surface S that has a non-zero slope (or a slope differing from the known reference slope) in the Y-direction, the light spot changes location on the quad cell detector as shown in FIG. 5. If a, b, c, and d represent the signal strengths of the four cells 50a–d, respectively, and k represents a calibration constant for the quad cell detector 50 which converts signal strength to change in spot location (e.g., in units of $\mu$m per millivolts or the like), then the change in Y-location of the light spot is given by $$\Delta y = k[(a+b)-(c+d)]$$

Similarly, if the surface S has a non-zero or non-reference slope in the X-direction, then the change in the X-location of the light spot is given by $$\Delta x = k[(a+c)-(b+d)]$$

The changes in spot location are directly related to the change in the angle of the reflected beam 44, which in turn is directly related to the change in surface slope. More particularly, where the converging optic 52 has a focal length $f$, the changes in spot location are given by $$\Delta x = f(\Delta \theta_x)$$

$$\Delta y = f(\Delta \theta_y)$$

where $\Delta \theta_x$ and $\Delta \theta_y$ are the changes in the reflected angle in the X- and Y-directions, respectively.

The changes in reflected angles are equal to twice the changes in the surface angles, which for very small surface angles closely approximate to twice the changes in the surface slopes, and hence $$\Delta p = \Delta \theta_x/2 \text{ and}$$

$$\Delta q = \Delta \theta_y/2,$$

where p is the surface slope in the X-direction and q is the surface slope in the Y-direction.

Thus, the changes in surface slopes may be calculated from the changes in spot locations as $$\Delta p = \Delta x/(2f)$$

$$\Delta q = \Delta y/(2f)$$

Accordingly, the changes in surface slopes in the X- and Y-directions can be deduced based on the signals from the cells 50a–d of the detector 50.

Figure 6:
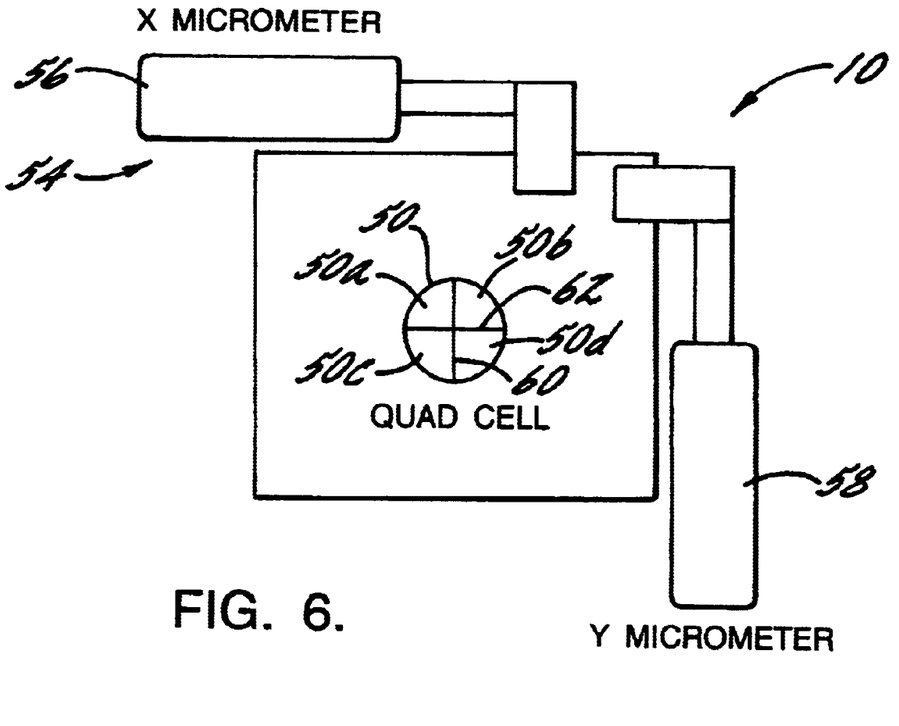
FIG. 6 is a schematic view of a mounting and calibration device for mounting the light detector.

With reference to FIG. 6, the apparatus 10 includes a micrometer mount 54 for calibrating the quad cell 50. The micrometer mount 54 includes an X-micrometer 56 and a Y-micrometer 58 which have their respective axes oriented normal to each other and so oriented that extension or retraction of the X-micrometer 56 causes the quad cell 50 to be advanced in a direction such that the light spot relatively moves parallel to the X-crosshair 60 that separates the cells 50a and 50c from the cells 50b and 50d. Likewise, extension or retraction of the Y-micrometer 58 causes the quad cell 50 to be advanced in a direction such that the light spot relatively moves parallel to the Y-crosshair 62 that separates the cells 50a and 50b from the cells 50c and 50d. The micrometers 56 and 58 are capable of accurately moving the quad cell 50 by very small incremental distances that are known. Thus, the known changes in light spot location can be correlated with the signals from the cells 50a–d in order to derive calibration factors for the quad cell 50.

Figure 7:
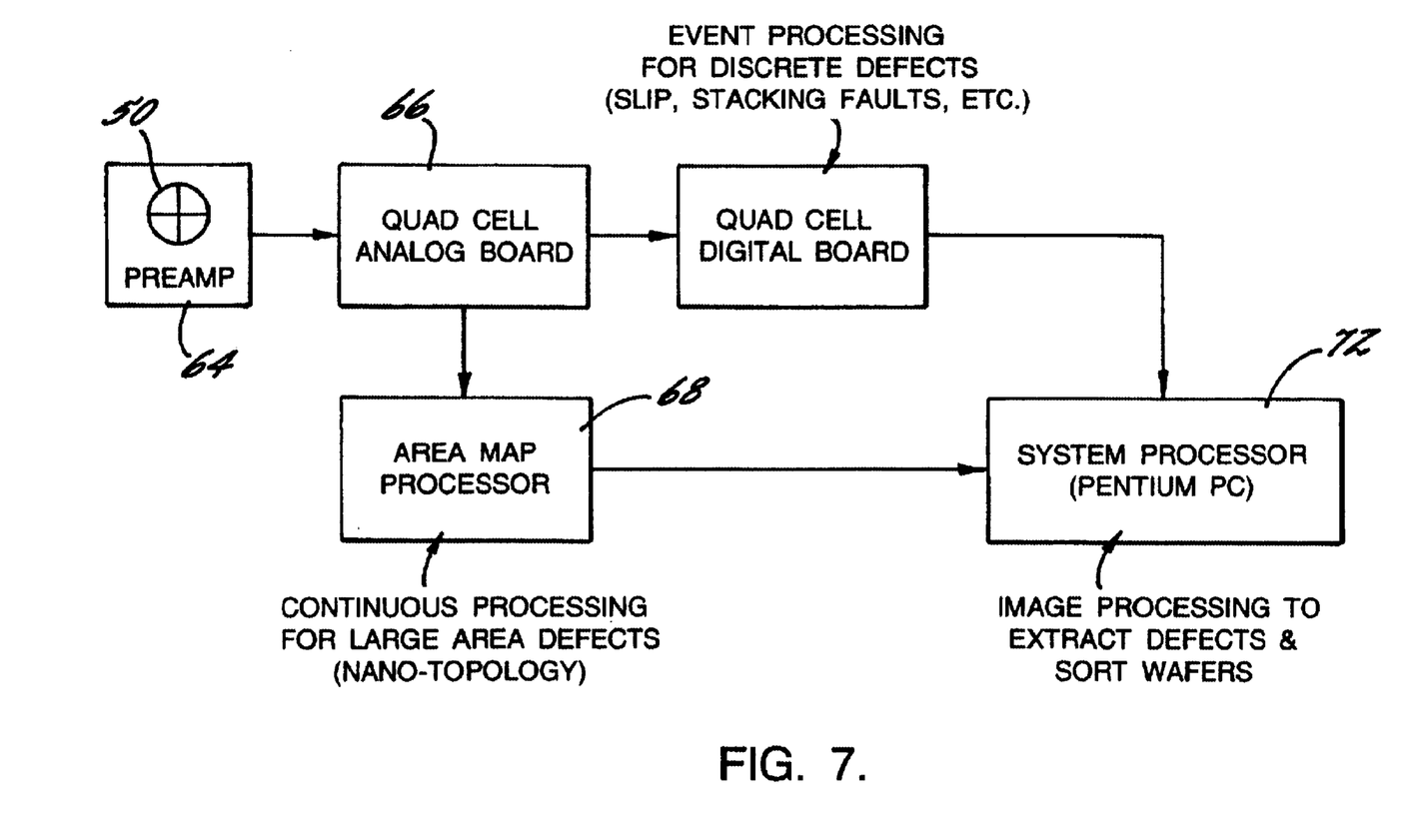
FIG. 7 is a block diagram showing a process for deriving a surface height map in accordance with the invention.

FIG. 7 depicts a block process diagram showing the signal processing and data manipulation in accordance with the invention. The signals from the quad cell 50 are passed through a pre-amplifier 64 and the amplified signals are fed to an analog board 66. The signals in analog form are then sent to an area map processor 68 which performs calculations as described above to deduce X- and Y-slopes for each of the pixels on the wafer surface so as to develop full surface maps of X- and Y-slopes. The processor 68 also uses the X- and Y-slopes to deduce a full surface height map, using an algorithm described in "A Line-Integration Based Method for Depth Recovery from Surface Normals" by Zhongquan Wu and Lingxiao Li, published in *Computer Vision, Graphics, and Image Processing*, volume 43, pages 53–66 (1988), the entire disclosure of which is incorporated herein by reference. Briefly, that algorithm deduces that the height z(i, j) of a pixel having the indices i and j may be determined by trapezoidal approximation of line integrals as $$z(i, j) = z_0 + \frac{1}{2}\left(\frac{q(i_0, j_0) + q(i_0, j)}{2} + \sum_{k=j_0+1}^{j-1} q(i_0, k)\right)\Delta y +$$

$$\frac{1}{2}\left(\frac{p(i_0, j_0) + p(i, j)}{2} + \sum_{k=i_0+1}^{i-1} p(k, j)\right)\Delta x +$$

$$\frac{1}{2}\left(\frac{p(i_0, j_0) + p(i, j_0)}{2} + \sum_{k=i_0+1}^{i-1} p(k, j_0)\right)\Delta x +$$

$$\frac{1}{2}\left(\frac{q(i, j_0) + q(i, j)}{2} + \sum_{k=j_0+1}^{j-1} q(i, k)\right)\Delta y.$$

where p and q are the surface slopes in the X- and Y-directions, $i_0$ and $j_0$ refer to a reference point having the height $z_0$, and $\Delta x$ and $\Delta y$ are the spacings between the pixels in the X- and Y-directions, respectively.

Figure 8:
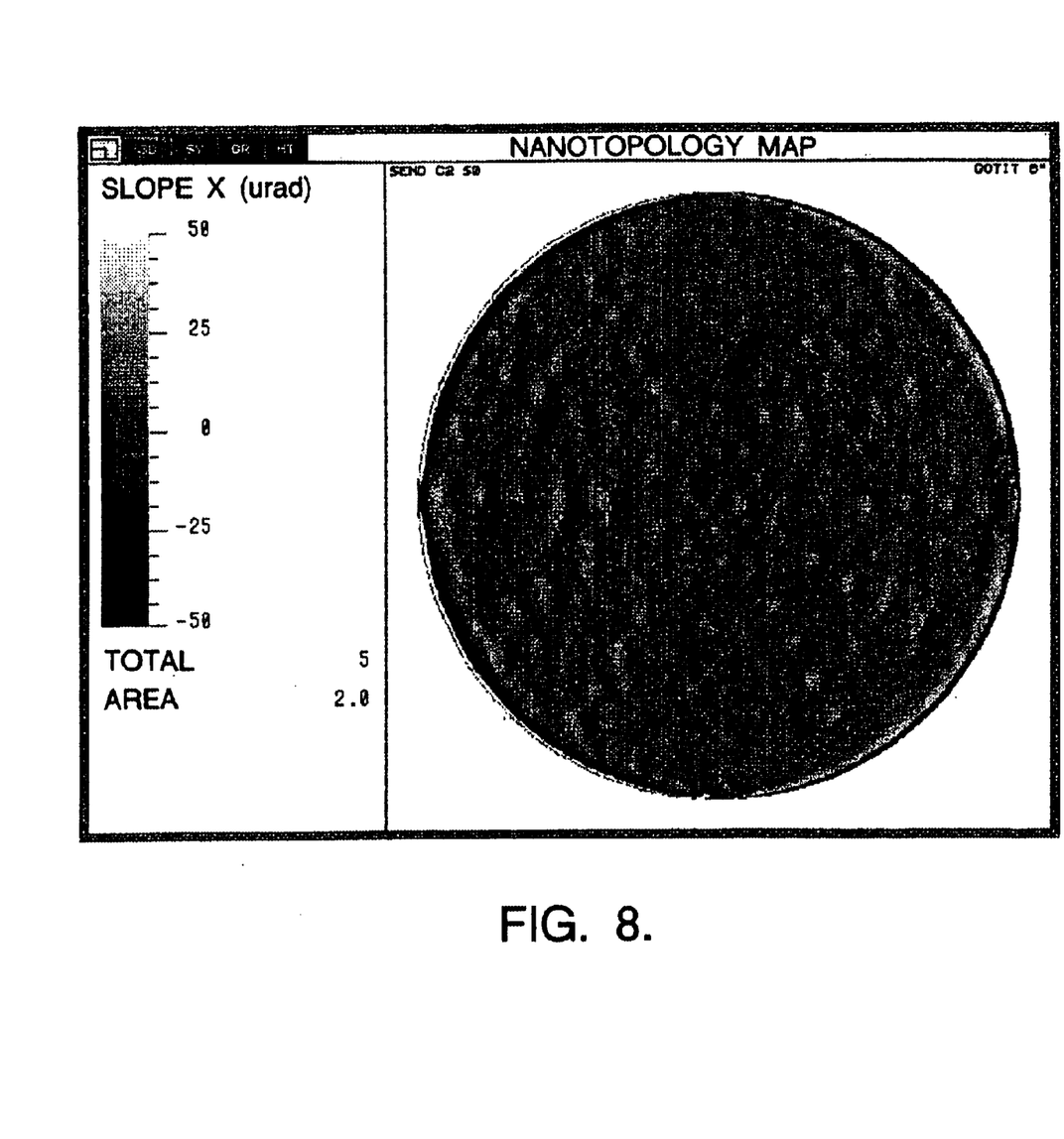
FIG. 8 shows a map of surface X-slope of a silicon wafer which was determined by an apparatus and method in accordance with the invention.
Figure 9:
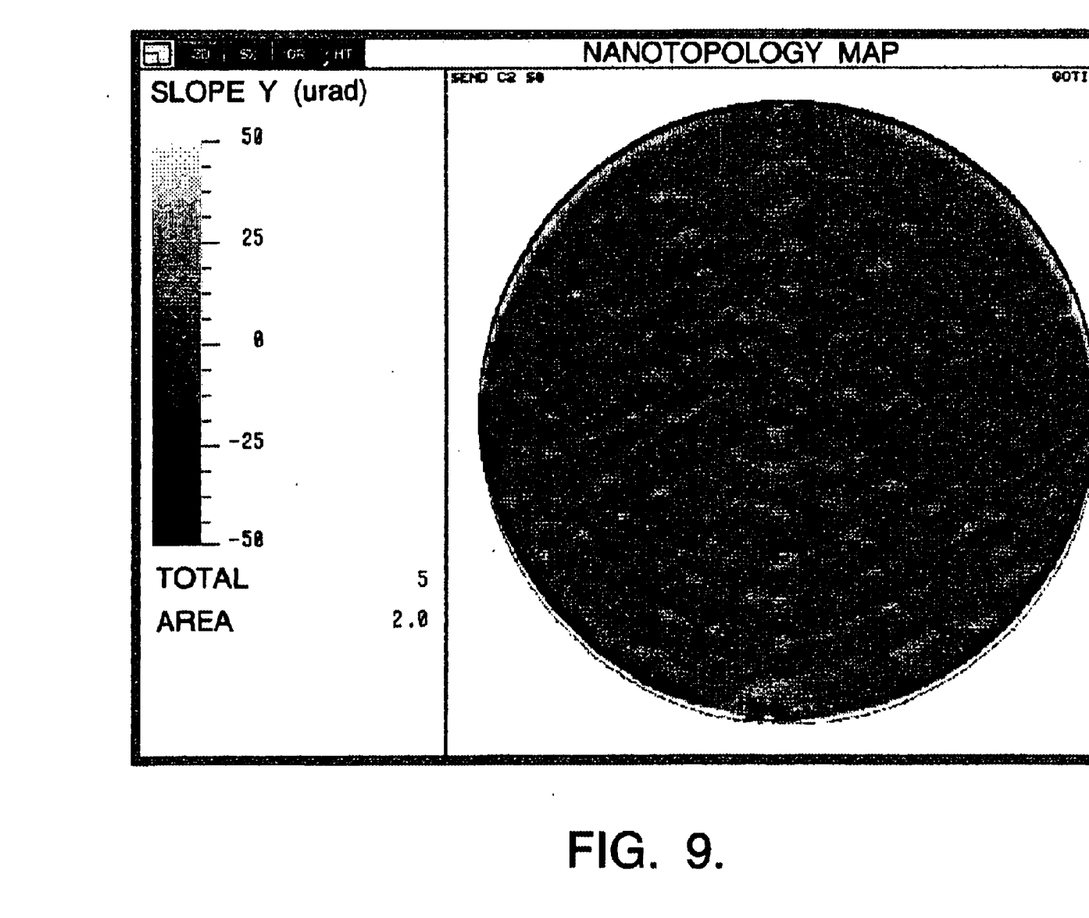
FIG. 9 shows a map of surface Y-slope for the silicon wafer of FIG. 8.
Figure 10:
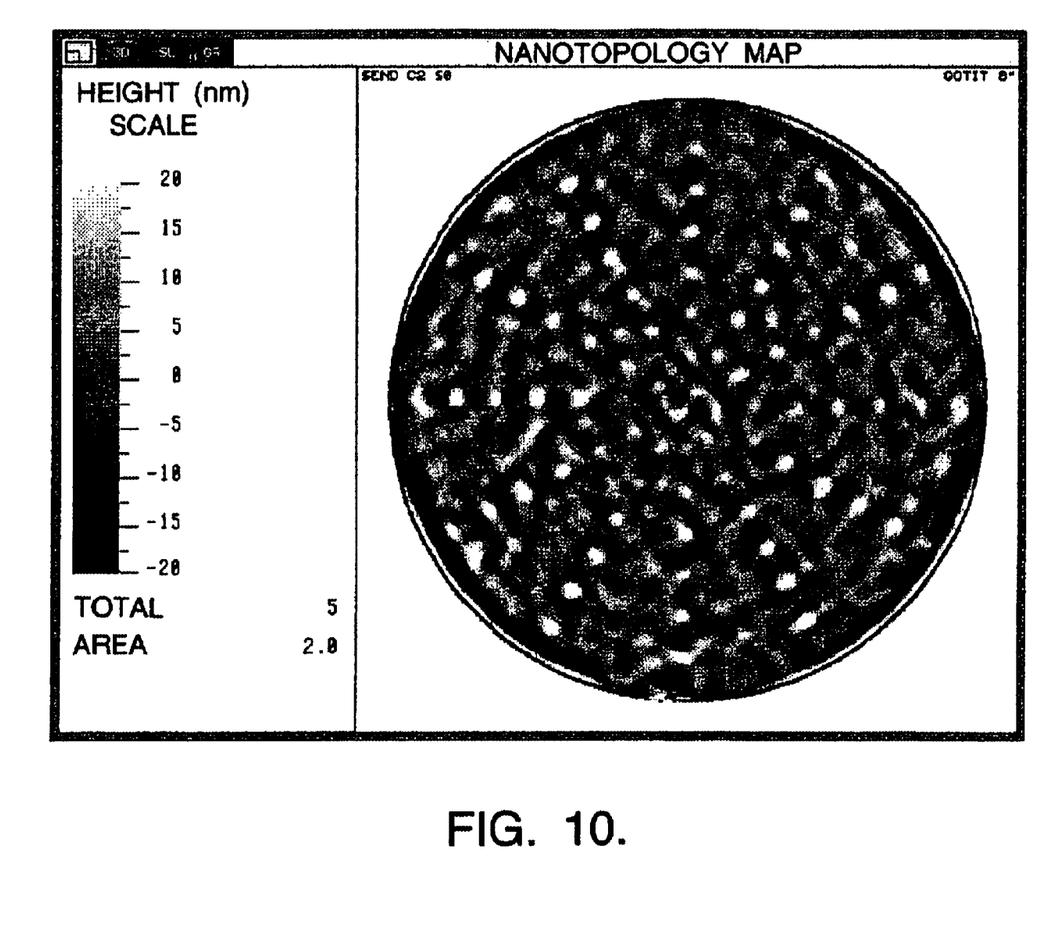
FIG. 10 shows a map of surface height for the silicon wafer of FIGS. 8 and 9 which was determined from the X- and Y-slope maps in accordance with the invention.

The digitized slope and height information from the area map processor 68 is fed to a system processor 72 that processes the information to produce images of the slope and height maps. FIGS. 8–11 depict slope and height maps produced from the scan of a silicon wafer by an apparatus in accordance with the invention. FIG. 8 shows a map of the X-slope which was determined using a map of 1024 by 1024 pixels each of 214 $\mu$m by 214 $\mu$m size distributed over the wafer surface. The incident beam had a spot size of 30 $\mu$m diameter. It can be seen that the map resolves surface slope down to changes on the order of plus or minus 1 $\mu$rad. FIG. 9 similarly depicts a map of the Y-slope, and FIG. 10 depicts the resulting height map constructed from the slope information. Surface height changes on the order of plus or minus 5–10 nm can readily be seen.

Figure 11:
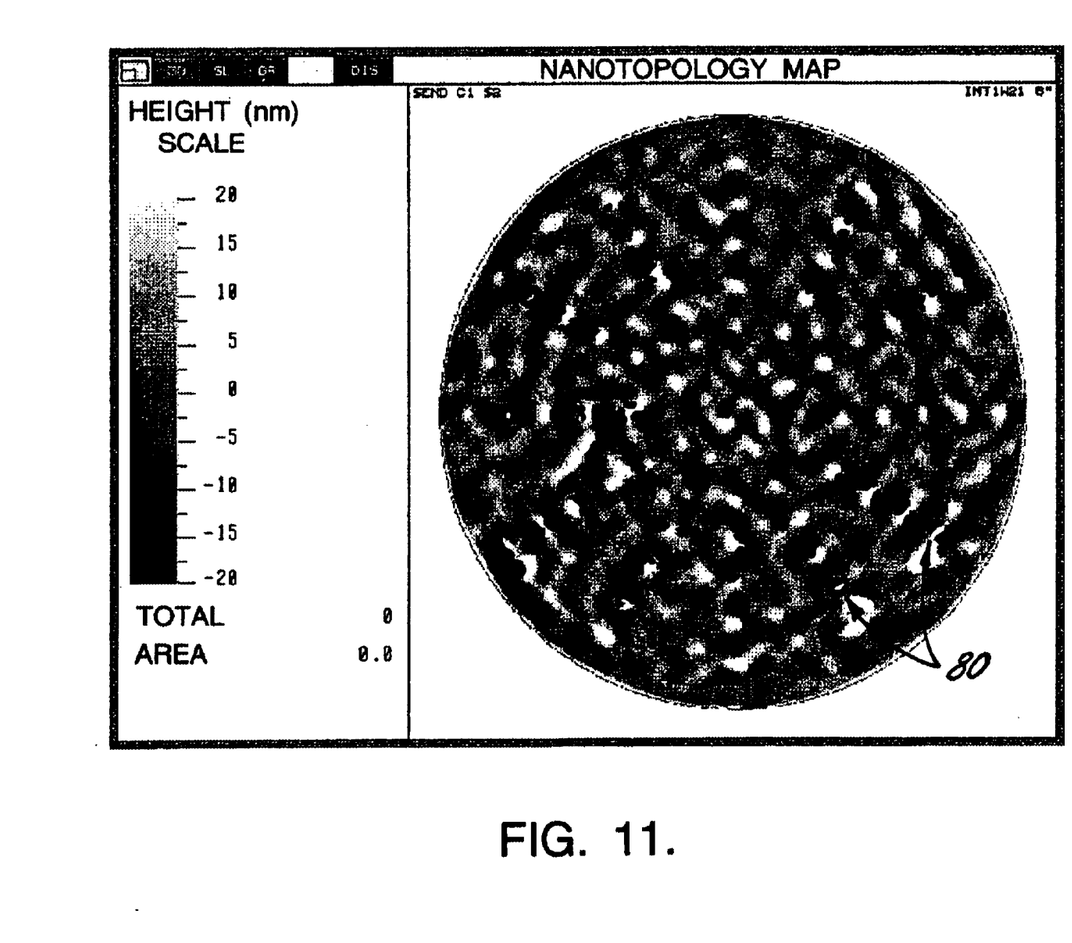
FIG. 11 shows a map similar to the map of FIG. 10, but indicating regions of the wafer surface which have been identified as having surface height deviations over a predetermined distance along the surface which exceed a predetermined threshold value.

Preferably, the system processor 72 is programmed to detect regions of the wafer surface having changes in surface height over a given distance along the surface that exceed a predetermined threshold value, using a defect detection algorithm. Thus, at each pixel location, the slope maps are used to calculate the surface height changes over a known distance in four directions, namely, the X-direction (defined as a 0° direction), the Y-direction (defined as a 90° direction), a +45° direction, and a −45° direction. The height changes are determined by averaging the slopes of several adjacent pixels on either side of the pixel in question, for example as $$\Delta H = \Delta L[p(i-1,j) + p(i,j) + p(i+1,j)]3,$$

where $\Delta L$ is the center-to-center distance along the surface occupied by the adjacent pixels, and p is the slope at each pixel in the X-direction. For instance, where the pixels are about 210 $\mu$m square, three adjacent pixels will occupy a distance $\Delta L$ of about 0.42 mm. The height changes are compared to the threshold, and if the height change in any of the four directions exceeds the threshold, the pixel is marked as a defect. These defect pixels can be indicated on a height map to obtain a visual indication of areas of excessive height change. FIG. 11 shows the height map of FIG. 10 with defect pixels indicated by solid shading 80. To obtain a spatial resolution of about 200 $\mu$m the grid points of the height map advantageously should be spaced apart by distances not substantially exceeding 200 $\mu$m.

The apparatus that has been illustrated and described herein for deducing surface slopes based on changes in the position of a beam specularly reflected from the surface employs an incident light beam 34 that impinges on the substrate surface at a near-normal incidence angle, for example, about 15° off normal. It is not essential for the practice of the present invention, however, that near-normal incidence angles be used. For incidence angles far from normal, there may be some degradation in the sensitivity of the detection device that senses the change in location of the reflected beam, particularly along the direction that is normal to the plane of incidence. Additionally, the equations relating the change in reflected beam location to the changes in surface slope given above may require some modification to account for the effect of the non-normal incidence angle. However, in other respects, the present invention is equally applicable to an apparatus providing non-normal incidence angle.

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An apparatus for mapping the topography of a surface of a substrate, comprising:

a light source adapted to produce an incident light beam and positioned to direct the incident beam to impinge on the surface and specularly reflect therefrom;

a scanning system operable to move at least one of the substrate and the incident beam so as to scan the incident beam along a plurality of scan lines each extending along the surface in a first direction and spaced apart from one another along a second direction, the incident beam impinging on the surface and being reflected therefrom to create a specularly reflected beam;

a light detector positioned to receive the specularly reflected beam, the detector comprising a plurality of light-sensitive cells arranged such that the detector is operable to provide signals indicative of a relative location of the specularly reflected beam on the detector along a first axis and indicative of a relative location of the specularly reflected beam on the detector along a second axis, the relative locations of the specularly reflected beam along the first and second axes being indicative of relative slopes of the surface along the first and second directions, respectively; and a processor operable to receive the signals from the detector and periodically sample and process the signals during each scan of the incident beam so as to create a plurality of sets of slope data corresponding to an array of points on the surface arranged in a grid defined by the first and second directions, each set of slope data comprising a relative slope along the first direction and a relative slope along the second direction for each point on the surface, whereby for each point of the array the processor determines relative slopes along both the first and second directions from the same scan of the incident beam at said point.

2. The apparatus of claim 1, wherein the scanning system and processor cooperate to define the grid of points as an orthogonal grid.

3. The apparatus of claim 2, wherein the processor is operable to calculate a relative surface height for each of the points of the array based on the relative slopes in the first and second directions, to deduce changes in surface height between each point and other points adjacent thereto in each of a plurality of different directions along the surface, and to identify as a defect region any point at which the change in surface height in any of the different directions exceeds a predetermined threshold.

4. The apparatus of claim 2, wherein the processor is operable to calculate changes in surface height between each point and other points adjacent thereto along the first direction, along the second direction, and along two additional directions that are angularly offset from the first and second directions.

5. The apparatus of claim 2, wherein the scanning system includes optics for scanning the beam along the first direction and a transport mechanism operable to move the substrate in the second direction.

6. The apparatus of claim 1, wherein the light detector comprises a multiple-cell detector having a plurality of adjacently arranged cells each of which produces a signal indicative of a light intensity striking the cell, and wherein the processor receives the signals from the cells and calculates a change in location of the specularly reflected beam by comparing the signals.

7. The apparatus of claim 6, wherein the light detector comprises a quad-cell detector having four cells arranged in quadrants oriented such that the signals from the cells are indicative of surface slopes in two orthogonal directions along the surface.

8. An apparatus for mapping the topography of a surface of a substrate, comprising:

a light source adapted to produce an incident light beam and positioned to direct the incident beam to impinge on the surface and specularly reflect therefrom;

a scanning system operable to move at least one of the substrate and the incident beam so as to move the incident beam in relation to the substrate such that the incident beam is impinged on the surface at a plurality of spaced-apart points to create a specularly reflected beam from each of the points, wherein the scanning system is operable to relatively move the incident beam across the surface along both a first direction and a second direction that is perpendicular to the first direction such that the array of points at which the changes in surface height are determined forms an orthogonal grid with the points being spaced apart from each other along the first direction and the second direction;

a light detector positioned to receive each of the specularly reflected beams, the detector being operable to provide a signal as a function of a change in location of each of the specularly reflected beams relative to a reference location; and a processor which receives the signal corresponding to each of the points on the surface and based on each signal calculates a change in slope of the surface at each point relative to a reference slope which corresponds to the reference location of the specularly reflected beam, the processor being operable to calculate changes in slope in the first direction and the second direction for each of the points and to calculate relative surface heights of the points based on the changes in slope, wherein the processor is operable to calculate a relative surface height at each point based on a line integration of the changes in surface slope along the orthogonal first and second directions, and wherein the processor is operable to calculate changes in surface height over a predetermined distance along the surface in each of a plurality of predetermined directions along the surface for each of the points, to compare the changes in surface height to predetermined thresholds at each point, and to identify as a defect region any point at which the change in surface height in any of the predetermined directions exceeds the predetermined threshold for that direction.

9. The apparatus of claim 8, wherein the processor is operable to calculate the changes in surface height along the first and second directions and two additional directions that are angularly offset from the first and second directions.

10. The apparatus of claim 9, wherein the light detector comprises a quad-cell detector having four cells each of which produces a signal indicative of an intensity of light striking the cell, the cells being arranged in quadrants oriented such that the signals from the cells are indicative of relative surface slopes in the first and second directions along the surface.

11. A method for mapping topography of a surface of a substrate, comprising:

impinging an incident light beam onto the surface at each of a plurality of points on the surface, the points being arranged in an array, the incident beam being reflected from the surface at each point so as to create a beam specularly reflected from the surface;

directing the specularly reflected beam from each point onto a surface of a detector;

for each point on the substrate surface, simultaneously determining a relative location of the specularly reflected beam on the detector surface along a first axis and a relative location of the specularly reflected beam on the detector surface along a second axis, the relative locations of the specularly reflected beam along the first and second axes being indicative of relative slopes of the substrate surface along first and second directions on the substrate surface, respectively; and integrating the relative slopes in the first and second directions for the plurality of points on the substrate surface so as to determine a relative surface height at each point, thereby deriving a height map for the substrate surface.

12. The method of claim 11, wherein the relative height of the surface at each point is calculated by performing a line integration of the changes in surface slopes along the first and second directions, the line integration being performed over the point for which the relative height is to be calculated and a plurality of points adjacent thereto.

13. The method of claim 11, wherein the directing step comprises converging the specularly reflected beam to a spot on a multiple-cell detector having a plurality of adjacently arranged cells each providing a signal indicative of an intensity of light striking the cell, and wherein the determining step comprises comparing the signals from the cells to determine a change in spot location on the detector and determining a change in orientation of the specularly reflected beam based on the change in spot location.

14. The method of claim 11, wherein the impinging step comprises using optics to periodically scan the incident beam along the first direction along the surface, and translating the substrate in the second direction such that the incident beam is scanned across the surface in lines which are spaced apart in the second direction.

15. The method of claim 14, wherein for each of the scans of the incident beam in the first direction along the surface, periodically the specularly reflected beam is detected and relative surface slopes are determined therefrom, whereby relative surface slopes are determined for a grid of surface points that are spaced apart in the first and second directions.

16. A method for mapping topography of a surface of a substrate, comprising:

scanning an incident light beam across the surface at a predetermined incident angle to create a beam specularly reflected from the surface, wherein the incident beam is impinged on the surface at points that are spaced apart by predetermined distances along each of a first direction and a second direction that is different from the first direction such that the points form a regular grid;

detecting the specularly reflected beam and determining for each of the points on the surface a change in orientation of the specularly reflected beam from a known reference orientation which corresponds to a reference value of surface slope;

calculating, based on the change in orientation of the specularly reflected beam, a change in surface slope from the reference value of surface slope for each of the points on the surface, wherein relative surface slopes are determined along both the first and second directions based on the change in orientation of the specularly reflected bean for each point;

calculating a relative height of the surface at each point based on the changes in surface slopes along the first and second directions at said point and at one or more points adjacent thereto, whereby a surface height map is produced; and calculating changes in surface height over a predetermined distance along the surface in each of a plurality of predetermined directions along the surface for each of the points, comparing the changes in surface height to predetermined thresholds at each point, and identifying as a defect region any point at which the change in surface height in any of the predetermined directions exceeds the predetermined threshold for that direction.

17. The method of claim 16, wherein the change in surface height over the predetermined distance is calculated at each point along the first and second directions and along two additional directions that are angularly offset from the first and second directions.

18. A method for identifying defect regions of a smooth surface of a substrate, comprising:

provinding a height map of the surface, the height map being defined by a grid of surface points spaced apart by predetermined distances along a first direction on the surface and along a second direction on the surface different from the first direction, each point having a relative surface height associated therewith;

calculating a change in surface height over a predetermined distance along the surface in each of a plurality of predetermined directions along the surface for each of the points;

comparing the change in surface height over the predetermined distance along each of the predetermined directions to a predetermined threshold at each point; and identifying as a defect region any point at which the change in surface height over the predetermined distance in any of the predetermined directions exceeds the predetermined threshold, wherein the height map is provided to have grid points spaced apart along the first and second directions by distances not substantially exceeding about 200 $\mu$m between adjacent grid points, whereby defect regions are resolved with a spatial resolution in the plane of the surface not exceeding about 200 $\mu$m.

* * * * *

UNITED STATES PATENT AND TRADEMARK OFFICE
CERTIFICATE OF CORRECTION

PATENT NO.    : 6,621,581 B1
DATED         : September 16, 2003
INVENTOR(S)   : Hunt et al.

It is certified that error appears in the above-identified patent and that said Letters Patent is hereby corrected as shown below:

<u>Title page,</u>
Item [75], Inventors, third inventor's address, "Clover, SC" should read
-- N. Smithfield, RI --; insert the following fourth Inventor,
 -- Brian Bernal, Broomfield, CO (US) --.

<u>Column 7,</u>
Line 15, before "3" insert a slash -- / --.

<u>Column 10,</u>
Line 54, "bean" should read -- beam --.

Signed and Sealed this

Twentieth Day of January, 2004

JON W. DUDAS
*Acting Director of the United States Patent and Trademark Office*